US010433806B2

(12) United States Patent
Tobita et al.

(10) Patent No.: US 10,433,806 B2
(45) Date of Patent: Oct. 8, 2019

(54) OPERATION DEVICE, CONTROL METHOD, AND X-RAY IMAGING UNIT

(71) Applicant: OMRON CORPORATION, Kyoto-shi, Kyoto (JP)

(72) Inventors: Kokichi Tobita, Unnan (JP); Koichi Furusawa, Okayama (JP)

(73) Assignee: OMRON Corporation, Kyoto-shi (JP)

( * ) Notice: Subject to any disclaimer, the term of this patent is extended or adjusted under 35 U.S.C. 154(b) by 0 days.

(21) Appl. No.: 15/575,874

(22) PCT Filed: Jul. 25, 2016

(86) PCT No.: PCT/JP2016/071774
§ 371 (c)(1),
(2) Date: Nov. 21, 2017

(87) PCT Pub. No.: WO2017/022550
PCT Pub. Date: Feb. 9, 2017

(65) Prior Publication Data
US 2018/0116624 A1    May 3, 2018

(30) Foreign Application Priority Data

Aug. 6, 2015  (JP) ................................. 2015-156475

(51) Int. Cl.
*A61B 6/00* (2006.01)
*H04Q 9/00* (2006.01)
*G08C 17/02* (2006.01)

(52) U.S. Cl.
CPC .............. *A61B 6/56* (2013.01); *A61B 6/4405* (2013.01); *A61B 6/467* (2013.01); *A61B 6/547* (2013.01);
(Continued)

(58) Field of Classification Search
CPC ......... A61B 6/56; A61B 6/4405; A61B 6/467; A61B 6/547; A61B 6/548
See application file for complete search history.

(56) References Cited

U.S. PATENT DOCUMENTS 5,206,894 A    4/1993  Makrinos et al.
2006/0244627 A1  11/2006  Kagermeier et al.
(Continued)

FOREIGN PATENT DOCUMENTS

JP    S63-97984 U    6/1988
JP    H5-344560 A    12/1993
(Continued)

OTHER PUBLICATIONS

English translation of Written Opinion of PCT/JP2016/071774 dated Feb. 15, 2018 from the International Searching Authority.
(Continued)

*Primary Examiner* — Amine Benlagsir
(74) *Attorney, Agent, or Firm* — Metrolex IP Law Group, PLLC

(57) ABSTRACT

An operation device (200) for wirelessly operating an X-ray imaging device (1) is held in a removable manner in a holder (100) included in the X-ray imaging device (1). The operation device (200) includes a control unit (211) that provides a notification when detecting that a predetermined condition is satisfied while the operation device (200) remains removed from the holder (100). This structure provides various notifications including a notification for preventing the operation device from being left or lost.

7 Claims, 7 Drawing Sheets

(52) U.S. Cl.
CPC .............. *A61B 6/548* (2013.01); *G08C 17/02* (2013.01); *H04Q 9/00* (2013.01)

(56) References Cited

U.S. PATENT DOCUMENTS

| | | | |
|---|---|---|---|
| 2013/0003938 A1* | 1/2013 | Watanabe | A61B 6/0457 378/195 |
| 2013/0094628 A1* | 4/2013 | Lalena | A61B 6/4283 378/98 |
| 2013/0147613 A1 | 6/2013 | Guo et al. | |
| 2014/0093040 A1* | 4/2014 | Omura | A61B 6/4405 378/62 |

FOREIGN PATENT DOCUMENTS

| | | | |
|---|---|---|---|
| JP | H06-185729 A | 7/1994 | |
| JP | H07-15461 U | 3/1995 | |
| JP | 2003-210445 A | 7/2003 | |
| JP | 2007-509638 A | 4/2007 | |
| JP | 2008-124681 A | 5/2008 | |
| JP | 201593581 A | 5/2015 | |

OTHER PUBLICATIONS

The (translated) International Search Report of PCT/JP2016/071774 dated Oct. 18, 2016.
The Australian Office Action dated Mar. 29, 2019 in a counterpart Australian patent application.
The Japanese Office Action (JPOA) dated May 21, 2019 in a counterpart Japanese patent application.

* cited by examiner

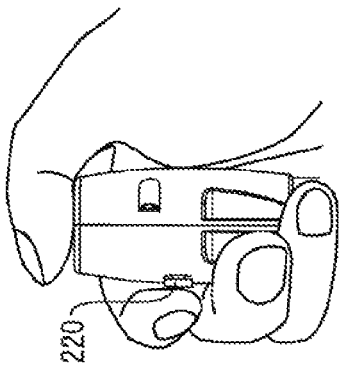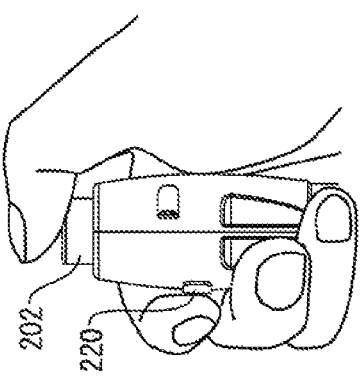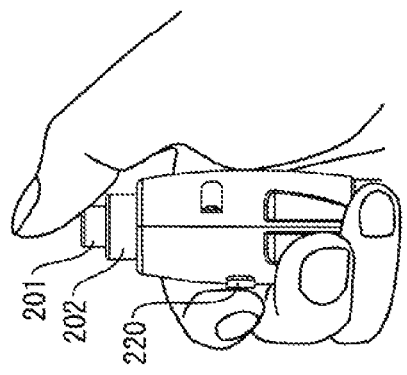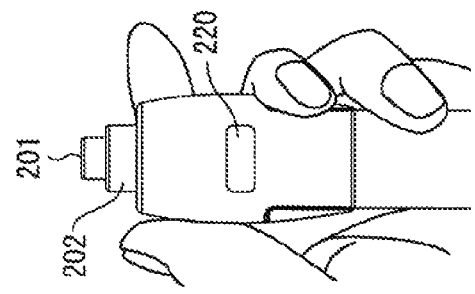

OPERATION DEVICE, CONTROL METHOD, AND X-RAY IMAGING UNIT

The present invention relates to an operation device, a control method, and an X-ray imaging unit for providing various notifications including a notification for preventing the operation device from being brought away.

BACKGROUND

An X-ray imaging device known in the art irradiates a patient with X-rays and detects the X-rays transmitted through the patient to generate images. The X-ray imaging device is usually operated using a wired operation device. The wired operation device is not lost easily.

An X-ray imaging device produced recently may be operated with a wireless operation device. For example, an X-ray imaging device described in Patent Literature 1 is operable with a remote controller using radio waves or infrared rays.

CITATION LIST

Patent Literature

Patent Literature 1: U.S. Pat. No. 5,206,894

SUMMARY

Technical Problem

However, the wireless remote controller described in Patent Literature 1 for either a portable or stationary main unit may be left after use, and may be lost. For example, the recent wireless remote controller may often be carried around in a hospital. The controller may thus often be left or lost. Although an advance notification of a battery run-down through a remote controller may be useful for the user, or a notification about an abnormality in the main unit through a remote controller may be useful for the remote controller, no remote controllers known in the art provide such notifications. This issue is not limited to an X-ray imaging device, and is common to any device with a wireless remote controller.

In response to the above issue, one or more aspects of the present invention are directed to an operation device, a control method, and an X-ray imaging unit for providing various notifications including a notification for preventing the operation device from being left or lost.

Solution to Problem

In response to the above issue, an operation device according to the above aspects of the present invention is used to wirelessly operate a main unit, and is held in a removable manner in a holding mechanism included in the main unit. The operation device includes a control unit that provides a notification when detecting that a predetermined condition is satisfied while the operation device remains removed from the holding mechanism.

Advantageous Effects

The above aspects of the present invention provide various notifications including a notification for preventing an operation device from being left or lost.

BRIEF DESCRIPTION OF THE DRAWINGS

FIGS. 5A to 5D are perspective views describing the operation procedure of the operation device according to the embodiment.

DETAILED DESCRIPTION

Figure 1:
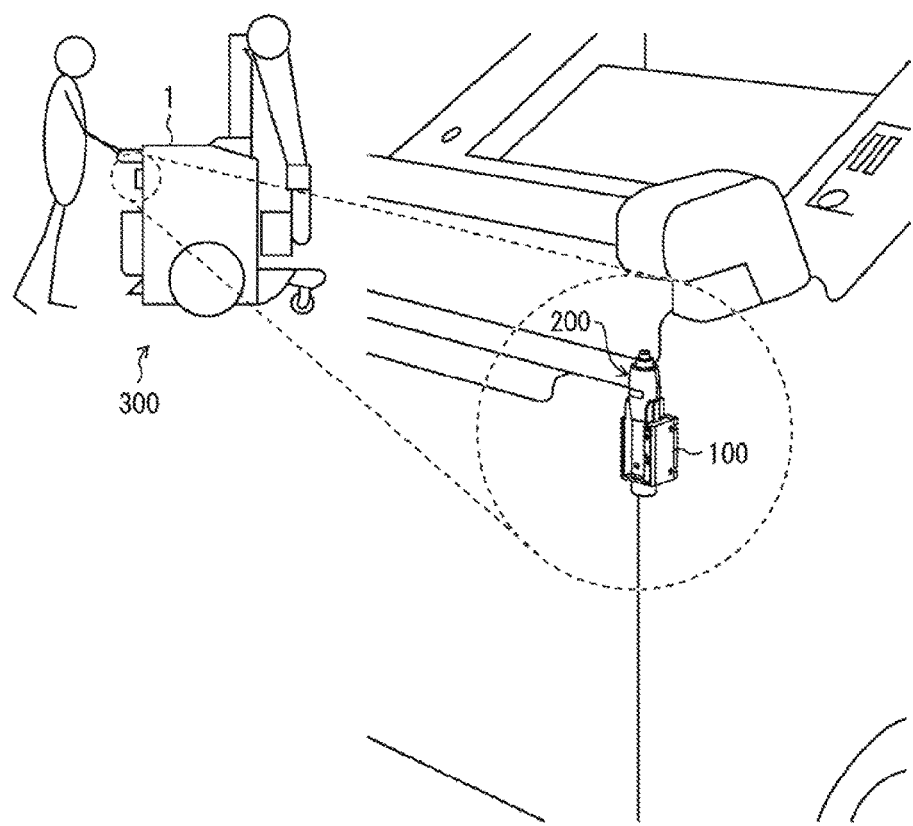
FIG. 1 is an external view of an X-ray imaging unit according to one embodiment.
Figure 2:
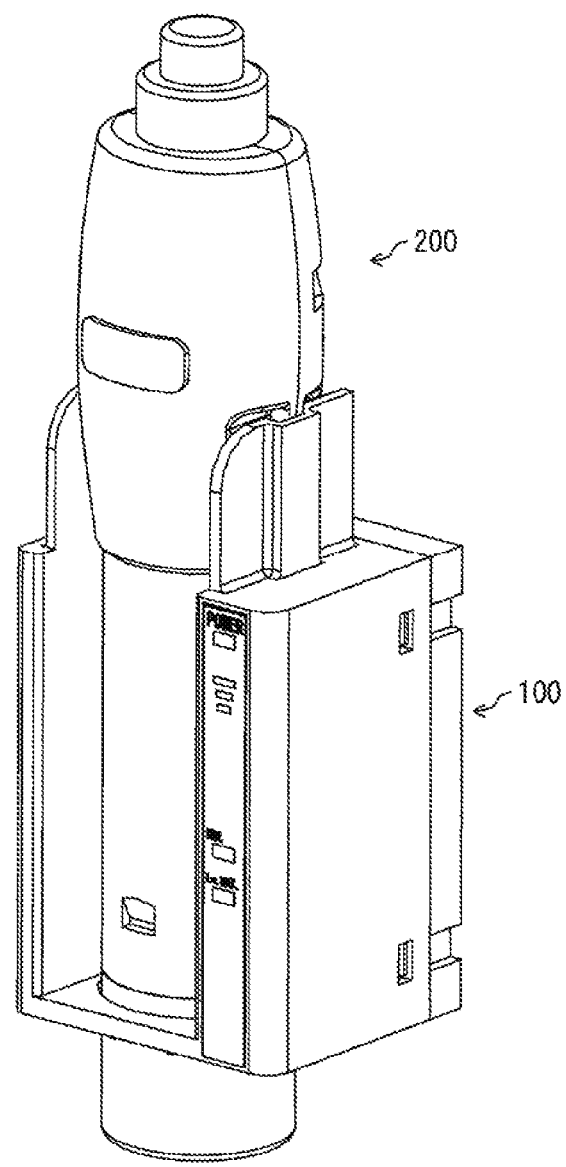
FIG. 2 is a perspective view of an operation device included in the X-ray imaging unit together with a holder according to the embodiment.

Embodiments of the present invention will now be described with reference to the drawings. FIG. 1 is an external view of an X-ray imaging unit according to one embodiment. FIG. 2 is a perspective view of an operation device included in the X-ray imaging unit together with a holder according to the present embodiment.

As shown in FIGS. 1 and 2, an X-ray imaging unit 300 irradiates a patient with X-rays and detects the X-rays transmitted through the patient to generate X-ray images. The X-ray imaging unit 300 includes an X-ray imaging device (main unit) 1, a holder (holding mechanism) 100, and an operation device 200. The X-ray imaging device 1 includes the holder 100 that holds the operation device 200 in a removable manner.

Figure 3:
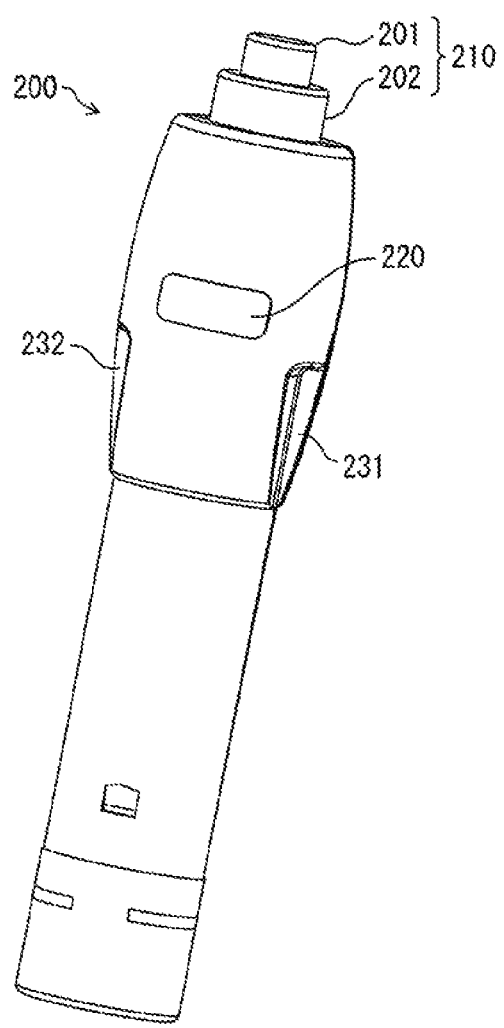
FIG. 3 is a perspective view of the operation device according to the embodiment.

FIG. 3 is a perspective view of the operation device according to the present embodiment. The operation device 200 is a remote controller for wirelessly operating the X-ray imaging device 1. The operation device 200 is substantially cylindrical. The operation device 200 includes a main switch 210 on its upper surface and an optional switch 220 in an upper portion of its peripheral surface to allow the user gripping the peripheral surface of the operation device 200 to operate the main switch 210 with a thumb and the optional switch 220 with a forefinger.

The main switch 210, which operates in two stages, includes first and second operation members 201 and 202 set at different home positions when not pressed by the user. The first operation member 201 has a longer stroke distance from its home position than the second operation member 202.

Figure 4:
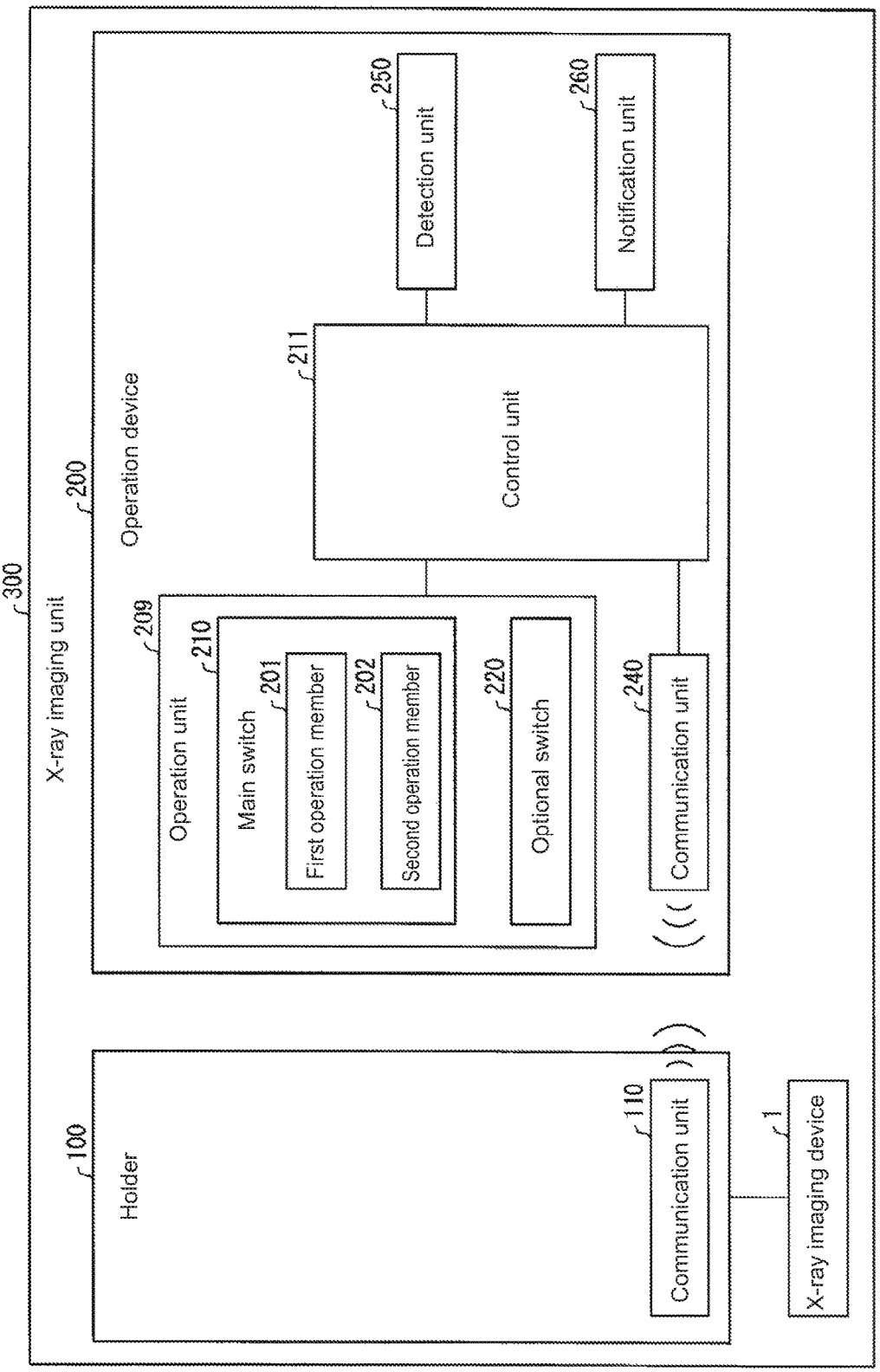
FIG. 4 is a functional block diagram of the X-ray imaging unit according to the embodiment.

FIG. 4 is a functional block diagram of the X-ray imaging unit according to the present embodiment. As shown in FIG. 4, the operation device 200 includes a control unit 211, which controls the entire operation device 200, an operation unit 209, a communication unit 240, a detection unit 250, and a notification unit 260.

The operation unit 209 includes the main switch 210 to be pressed to output an instruction for X-ray imaging to the X-ray imaging device 1, and the optional switch 220 to be pressed to output, to the X-ray imaging device 1, an instruction for turning on or off a lighting instrument included in the X-ray imaging device 1.

The main switch 210 includes the first and second operation members 201 and 202. When the first operation member 201 is pressed to the home position of the second operation member 202, an instruction for charging an X-ray imaging circuit is output (through the holder 100) to the X-ray imaging device 1 (refer to FIGS. 5A to 5C). When the first operation member 201 remains in the pressed state for a predetermined time, the X-ray imaging circuit is fully charged and becomes ready for imaging. When both the first operation member 201 and the second operation member 202 are pressed to the full-stroke position, an instruction for X-ray imaging is output (through the holder 100) to the X-ray imaging device 1 (refer to FIG. 5D).

Figure 6:
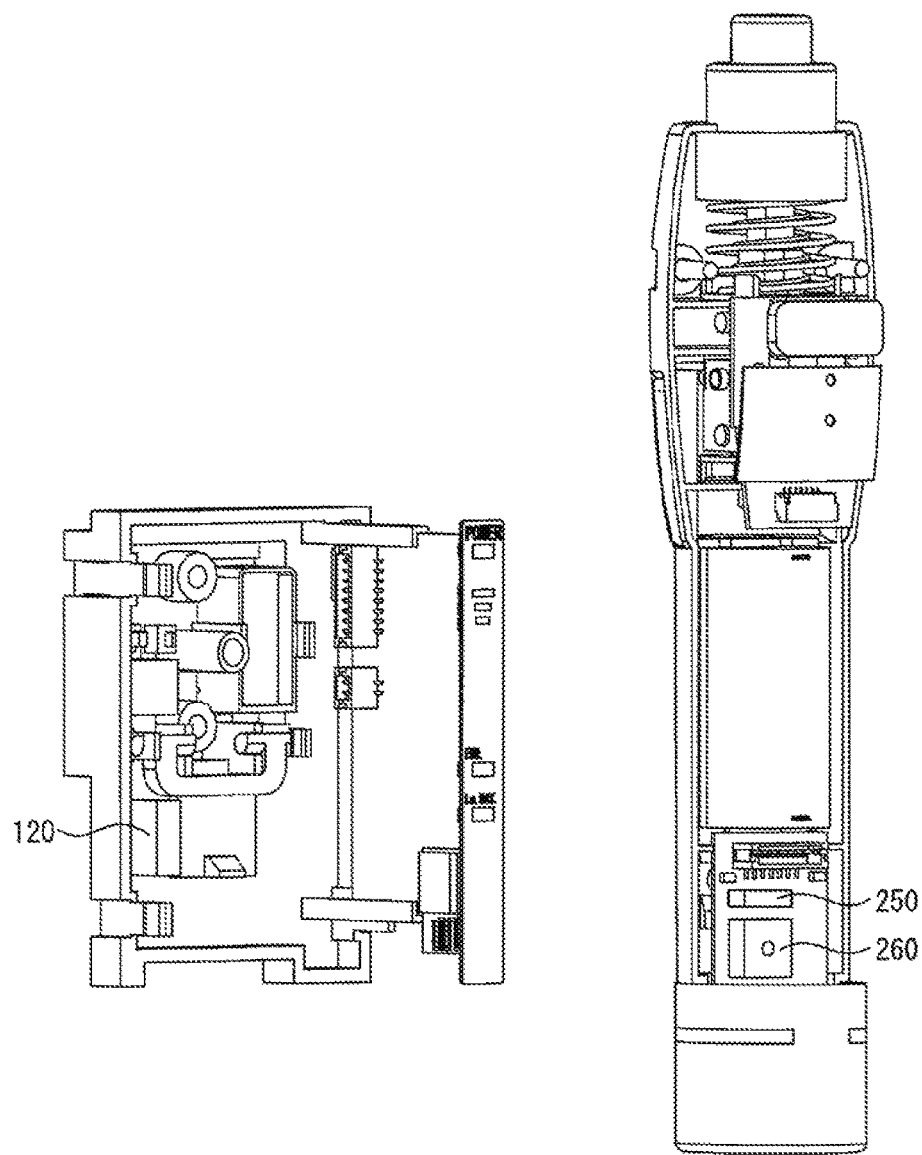
FIG. 6 is a diagram showing the internal structure of the operation device and the holder according to the embodiment.

The detection unit 250 determines whether the operation device 200 is mounted on the holder 100. For example, the operation device 200 includes a Hall integrated circuit (IC) as the detection unit 250 as shown in FIG. 6. The holder 100 includes a magnet 120. The Hall IC senses the magnet 120 included in the holder when the operation device 200 is mounted on the holder 100.

In some embodiments, the operation device 200 and the holder 100 may each include electrodes, which can contact with each other when the operation device 200 is mounted on the holder 100. Upon sensing the contact between the electrodes, the operation device 200 may determine that the operation device 200 is mounted on the holder 100.

The communication unit 240 transmits and receives data to and from the communication unit 110 included in the holder 100. More specifically, the communication unit 240 transmits a signal for an operation performed by the operation unit 209 and a detection result from the detection unit 250 to the holder 100. The notification unit 260 may be, for example, a sound-emitting device or a light-emitting device (LED), which provides a notification using sound or light.

The control unit 211 causes the notification unit 260 to provide a notification when a predetermined time T1 passes from when the operation device 200 is removed from the holder 100. More specifically, the control unit 211 starts measuring the time when the detection unit 250 detects an unmounted state in which the operation device 200 is not mounted on the holder 100. The predetermined time T1 is, for example, about 10 minutes.

When providing a notification, the control unit 211 continues the notification for a predetermined time T2, and then disables any operation to be input from the operation unit 209 at the same time as when providing the notification or after a predetermined time T3 passes from when the notification is stopped.

When the detection unit 250 detects a mounted state in which the operation device 200 is mounted on the holder 100 after the operation device 200 is previously removed from the holder 100, the control unit 211 stops measuring the time by resetting the time, and also stops any notification being performed. When an operation through the operation unit 209 has been disabled, the control unit 211 enables the operation. Although the notification is provided continuously for the predetermined time T2 in the present embodiment, the notification may be provided until the detection unit 250 detects a mounted state irrespective of the notification duration.

When the operation unit 209 is operated before the predetermined time T1 passes after the operation device 200 is removed from the holder 100, the control unit 211 resets the time measurement. This delays the notification to be provided by the notification unit 260 and enables continuous use of the operation device 200. The predetermined time T1 may not be limited to the above specified time, and may be any appropriate time for which the operation device 200 is to be used continuously.

Figure 7:
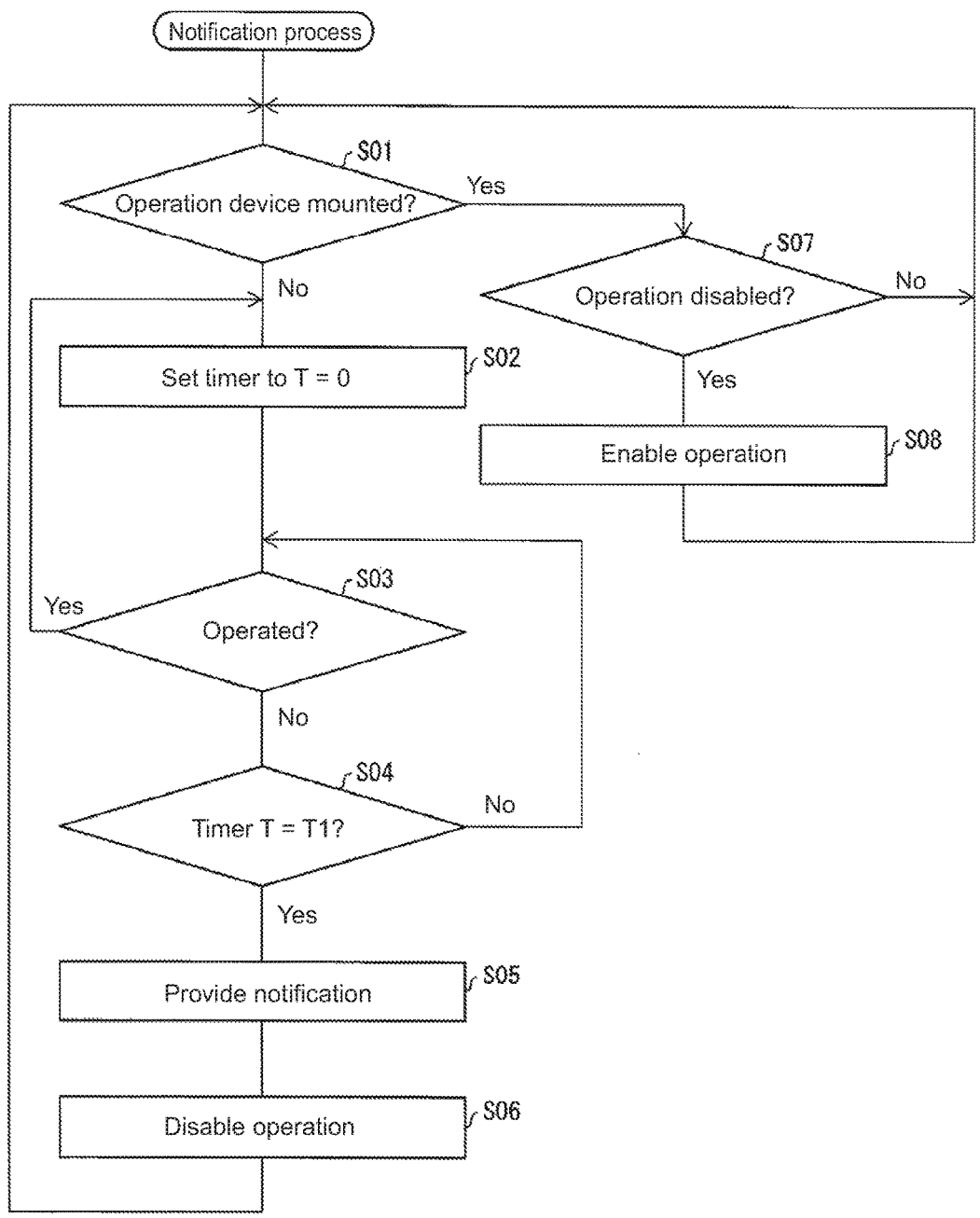
FIG. 7 is a flowchart showing an example notification process according to the embodiment.

FIG. 7 is a flowchart showing an example notification process according to the present embodiment. As shown in FIG. 7, the control unit 211 included in the operation device 200 causes the detection unit 250 to determine whether the operation device 200 has been mounted on the holder 100 (step S01). When detecting no operation device 200 mounted on the holder 100, the control unit 211 advances the processing to step S02. When detecting the operation device 200 mounted on the holder 100, the control unit 211 advances the processing to step S07.

In step S02, the control unit 211 starts measuring the time using a timer set to T=0. The control unit 211 then determines whether the operation unit 209 has been operated (step S03). When determining that the operation unit 209 has been operated, the control unit 211 returns the processing to step S02, and otherwise advances the processing to step S04.

In step S04, the control unit 211 determines whether the timer has reached T=T1. When the timer has reached T=T1, the control unit 211 advances the processing to step S05, and otherwise returns the processing to step S03.

In step S05, the control unit 211 provides a notification and disables any operation through the operation unit 209. The operation may be disabled at the same time as when the notification is provided or after the predetermined time T3 passes from when the notification is stopped to allow time for the user to remount the operation device 200 onto the holder 100.

The processing in step S07 is performed when the operation device 200 is determined to have been mounted on the holder 100. In step S07, the control unit 211 determines whether an operation through the operation unit 209 is disabled. When determining that the operation through the operation unit 209 is disabled, the control unit 211 advances the processing to step S08, and otherwise returns the processing to step S01.

In step S08, the control unit 211 enables the operation through the operation unit 209, and returns the processing to step S01.

As described above, the operation device 200 according to the present embodiment is held in the holder 100 included in the X-ray imaging device 1 in a removable manner, and is used to wirelessly operate the X-ray imaging device 1. The operation device 200 includes the control unit 211, which provides a notification using an alarm sound when detecting that the operation device 200 remains removed from the holder 100 continuously for the predetermined time T1.

This structure allows the user and other persons involved to be notified that the operation device 200 has not been remounted to the holder 100 for a period longer than the time expected for normal use of the operation device 200, and also to determine the current location of the operation device 200. The structure allows the user and other persons involved to early and easily find that the operation device 200 has been brought away.

This structure disables the operation at the same time as or after the notification is provided, and thus can further prevent a third party who may have brought away the operation device 200 from operating the device.

Although the notification is provided using an alarm sound when the operation device is determined to remain removed from the holder 100 continuously for the predetermined time T1 in the present embodiment, the notification may be provided when a predetermined condition is determined to be satisfied while the operation device 200 remains removed from the holder 100.

This structure allows the user to be notified by the notification that the operation device 200 remains removed from the holder 100 for prompting the user to remount the operation device 200 onto the holder 100. This prevents the operation device 200 from being left or lost.

When the operation unit 209 is operated before the predetermined time T1 passes from when the operation device 200 is removed from the holder 100, the time measurement is reset to delay the notification to be provided by the notification unit 260. In some embodiments, the holder may have a reset button for resetting the time measurement at a less visible position, or for example, at an edge of the back surface or on the bottom. In this structure, the holder 100 may transmit an instruction for resetting the measurement to the operation device 200 through the communication unit 110.

The notification unit 260 provides the notification based on detection performed by the detection unit 250 as to whether the operation device 200 has been mounted on the holder 100. In place of or in addition to this structure, the notification unit 260 may provide a notification when detecting no more communication with the holder 100 or with the X-ray imaging device 1 based on the strength of radio waves between the operation device 200 and the holder 100.

The notification unit 260 may be included in at least one of the X-ray imaging device 1 and the holder 100. In this structure, the communication unit 240 included in the operation device 200 communicates with the X-ray imaging device 1 (holder 100) to cause the notification unit 260 to provide a notification.

The communication unit 240 may also communicate with an information processing device or a portable terminal other than the holder 100 or the X-ray imaging device 1 to provide a notification.

The operation device 200 rechargeable when mounted on the holder 100 may provide a notification for the information described below. When the charged power in the operation device 200 decreases below a predetermined level while the operation device 200 remains removed from the holder 100, the notification unit 260 may provide a notification of the power decrease.

The notification unit 260 may also provide a notification when the X-ray imaging device 1 has an abnormality while the operation device 200 remains removed from the holder 100. In this case, information indicating the abnormality may be wirelessly transmitted from the X-ray imaging device 1 to the operation device 200 to cause the notification unit 260 to provide the notification.

Implementations Using Software

Each functional block of the operation device 200 (in particular the control unit 211) may be achieved using a logic circuit (hardware) included in, for example, an integrated circuit (IC chip), or using software implemented by a central processing unit (CPU).

When the functional blocks are achieved by using software, the operation device 200 includes a CPU, which executes instructions included in a program or software to achieve the functions, a read-only memory (ROM) or a storage device (hereinafter referred to as a storage medium), which stores the program and various data readable by a computer (or CPU), and a random access memory (RAM), into which the program is expanded. The computer (or CPU) reads the program from the storage medium, and executes the program to achieve one or more aspects of the present invention. The storage medium may be a non-transitory tangible medium, such as a tape, a disk, a card, a semiconductor memory, or a programmable logic circuit. The program may be provided via any transmission medium that can transmit the program to the computer (such as a communication network or a broadcast wave). One or more embodiments of the present invention may be implemented using programs that are electronically transmitted in the form of data signals carried by carrier waves.

SUMMARY

As described above, an operation device according to one aspect of the present invention is used to operate a main unit wirelessly, and is held in a removable manner in a holding mechanism included in the main unit. The operation device includes a control unit that provides a notification when detecting that a predetermined condition is satisfied while the operation device remains removed from the holding mechanism.

The above structure allows a notification to be provided to the user when a predetermined condition is satisfied while the operation device remains removed from the holding mechanism for prompting the user to remount the operation device onto the holding mechanism. This prevents the operation device from being left or lost, and allows various notifications to be provided. The operation device with the above structure thus provides various notifications including a notification for preventing the operation device from being left or lost.

The control unit included in the operation device according to the aspect of the present invention may provide the notification when detecting that the operation device remains removed from the holding mechanism continuously for a predetermined time as the predetermined condition.

The control unit included in the operation device according to the aspect of the present invention further provides the notification using an alarm sound.

The above structure allows the user or other persons involved staying away from the operating site of the device to early find that the operation device has been brought away.

The control unit included in the operation device according to the aspect of the present invention further disables an operation through the operation device at the same time as when the notification is provided or after the notification is provided.

The above structure can prevent a third party who may have brought away the operation device from operating the device.

The control unit included in the operation device according to the aspect of the present invention further enables the operation when the operation device is remounted onto the holding mechanism after the operation is disabled.

The operation device with this structure to be used as normal under the control of the user.

The control unit included in the operation device according to the aspect of the present invention further resets, when detecting an operation through the operation device before the predetermined time passes, time measurement for the operation device that remains removed from the holding mechanism.

The above structure allows continuous use of the operation device without remounting the operation device onto the holding mechanism.

The operation device according to the aspect of the present invention further includes a communication unit that wirelessly communicates with the holding mechanism or with the main unit. The control unit provides the notification when detecting no more communication with the holding mechanism or with the main unit.

The above structure allows the notification to be provided when the operation device is brought away beyond the range in which the operation device is communicable. This allows the user to find that the operation device has been brought away before being brought to a distant location.

An X-ray imaging unit according to another aspect of the present invention includes the operation device and an X-ray imaging device that detects X-rays to generate an X-ray image. The X-ray imaging device is the main unit.

The X-ray imaging unit with the above structure provides various notifications including a notification for preventing the operation device from being left or lost.

A notification method according to another aspect of the present invention is implemented in an operation device for wirelessly operating a main unit and being held in a removable manner in a holding mechanism included in the main unit. The notification method includes providing a notification when detecting that the operation device remains removed from the holding mechanism continuously for a predetermined time.

The above notification method provides various notifications including a notification for preventing the operation device from being left or lost.

The embodiments disclosed herein should not be construed to be restrictive, but may be modified within the spirit and scope of the claimed invention. The technical features disclosed in different embodiments may be combined in other embodiments within the technical scope of the invention.

REFERENCE SIGNS LIST

1 X-ray imaging device (main unit)
100 holder (holding mechanism)
110, 240 communication unit
200 operation device
209 operation unit
260 notification unit
210 main switch
211 control unit
220 optional switch
250 detection unit
300 X-ray imaging unit

The invention claimed is:

1. An operation device for wirelessly operating an X-ray imaging device configured to detect X-rays to generate an X-ray image, the operation device being configured to be held in a removable manner in a holding mechanism included in the X-ray imaging device, the operation device comprising a detector integrated circuit, wherein:
the detector circuit is configured to sense a magnet included in the holding mechanism to detect that the operation device is mounted on the holding mechanism;
a controller central processor is programmed to perform operations comprising first operations to provide a notification in response to the detector circuit detecting that a predetermined condition is satisfied while the operation device remains removed from the holding mechanism;
the controller central processor is further programmed to perform the operations further comprising second operations to provide the notification in response to the detector circuit detecting that the operation device remains removed from the holding mechanism continuously for a predetermined time as the predetermined condition; and
the operation device further comprises a reset button for resetting a measurement of a time for which the operation device continuously remains removed from the holding mechanism.

2. The operation device according to claim 1, wherein the controller central processor is further programmed to perform the operations further comprising third operations to provide the notification using an alarm sound.

3. The operation device according to claim 1, wherein the controller central processor is further programmed to perform the operations further comprising fourth operations to disable an operation through the operation device at the same time as when the notification is provided or after the notification is provided.

4. The operation device according to claim 3, wherein the controller central processor is further programmed to perform the operations further comprising fifth operations to enable the operation when the operation device is remounted onto the holding mechanism after the operation is disabled.

5. The operation device according to claim 1, wherein the controller central processor is further programmed to perform the operations further comprising sixth operations to reset, when detecting an operation through the operation device before the predetermined time passes, the measurement of the time for which the operation device remains removed from the holding mechanism.

6. The operation device according to claim 1, wherein the controller central processor is further programmed to perform the operations further comprising:
operation as a communication transceiver configured to wirelessly communicate with the holding mechanism or with the X-ray imaging device, and
the controller central processor is further programmed to perform the operations further comprising providing the notification when detecting no more communication with the holding mechanism or with the X-ray imaging device.

7. A control method implemented in an operation device, the control method comprising:
wirelessly operating an X-ray imaging device configured to detect X-rays to generate an X-ray image, wherein the operation device being configured to be held in a removable manner in a holding mechanism included in the X-ray imaging device;
sensing a magnet included in the holding mechanism to detect that the operation device is mounted on the holding mechanism;
providing a notification in response to detecting that a predetermined condition is satisfied while the operation device remains removed from the holding mechanism;
providing the notification in response to detecting that the operation device remains removed from the holding mechanism continuously for a predetermined time as the predetermined condition; and
resetting, via a reset button, a measurement of a time for which the operation device continuously remains removed from the holding mechanism.

* * * * *